(12) United States Patent
Watanabe

(10) Patent No.: US 6,172,749 B1
(45) Date of Patent: *Jan. 9, 2001

(54) METHOD OF AND APPARATUS FOR DETECTING A SURFACE CONDITION OF A WAFER

(75) Inventor: Masao Watanabe, Tokyo (JP)

(73) Assignee: Advantest Corporation, Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/018,177

(22) Filed: Feb. 3, 1998

(30) Foreign Application Priority Data

Feb. 5, 1997 (JP) .................................................. 9-022584

(51) Int. Cl.[7] .................................................. G01N 21/00
(52) U.S. Cl. ...................................... 356/237.4; 356/237.5
(58) Field of Search ........................ 324/750; 356/237.4, 356/237.5

(56) References Cited

U.S. PATENT DOCUMENTS

| 4,297,032 | * | 10/1981 | Temple | 356/239 |
| 4,401,893 | * | 8/1983 | Dehuysser | 250/572 |
| 5,235,400 | * | 8/1993 | Terasawa et al. | 356/237.5 |
| 5,245,403 | * | 9/1993 | Kato et al. | 356/237.4 |

FOREIGN PATENT DOCUMENTS 0 503 236   9/1992  (EP) .

OTHER PUBLICATIONS

WPI Abstract, AN 95–349124/199545, JP 7–239307, Sep. 12, 1995.
WPI Abstract, AN 95–149731/199520, JP 7–072092, Mar. 17, 1995.

* cited by examiner

Primary Examiner—Robert Kim
(74) Attorney, Agent, or Firm—Oblon, Spivak, McClelland, Maier & Neustadt, P.C.

(57) ABSTRACT

An apparatus for detecting a surface condition of a wafer can be incorporated in a wafer production system. The apparatus has a laser beam source for emitting a laser beam having a wavelength for transmission through the wafer. The laser beam source is positioned to apply the laser beam to the wafer from a reverse side thereof such that the laser beam undergoes total reflection from a surface of the wafer for thereby producing near-field leakage light on the surface of the wafer. Scattered light generated by the near-field leakage light is observed to detect a surface condition of the wafer. A method of detecting a surface condition of a wafer is also disclosed.

17 Claims, 6 Drawing Sheets

METHOD OF AND APPARATUS FOR DETECTING A SURFACE CONDITION OF A WAFER

BACKGROUND OF THE INVENTION

1. Field of the Invention

The present invention relates to a method of and an apparatus for optically inspecting a semiconductor wafer for particular contamination.

2. Description of the Related Art

Processes for fabricating high-density integrated circuits (ICs) on Si wafers and GaAs wafers are-becoming more and more sophisticated year after year, and those integrated circuits are also becoming smaller and smaller in size. For these reasons, the contamination of semiconductor wafers with fine particles poses a serious problem. Because interconnections on semiconductor wafers have a width less than 5 μm, the performance of IC chips is lowered and the yield of IC chips is reduced by contamination caused by fine particles whose size ranges from 0.5 μm to several μm, and particularly contamination by fine metal particles. It is therefore necessary to inspect wafers for particular contamination at various stages of semiconductor wafer fabrication. It is of importance to quickly remove wafers from the fabrication process and inspect the removed wafers, and also to inspect wafers according to nondestructive testing.

For example, for detecting a single fine particle having a size of 0.5 μm on an 8-inch wafer, it is necessary to observe $10^6$ spots on the wafer in its entirety because of the size of a detectable observation field that is available. Due to the many observation spots, it is highly time-consuming to inspect the wafer, and inspection processes that can meet the requirements for quick observation are limited.

Prerequisites for analyzing wafers for fine particles thereon include freedom from contamination of the wafers and also freedom from damage to the wafers. It is also important for such a wafer analysis to determine the number, sizes, and types of fine particles that are present on the wafers.

One inspection process that is under consideration at present is to detect Mie scattering by fine particles for thereby detecting the fine particles. It will take more than 10 minutes to scan a wafer in its entirety according to the Mie scattering inspection process.

When a fine particle is detected, it is customary to identify the type of the detected fine particle. General elemental analytic processes for identify the type of a fine particle include an EPMA (Electron Probe Micro Analysis) process and an AES (Auger Electron Spectroscopy) process. Either of these elemental analytic processes requires that the wafer under inspection be placed in vacuum container and each particle be analyzed for its type for a period of about 5 minutes.

According to those elemental analytic processes, it is necessary to irradiate the wafer with an electron beam having an energy level of 10 keV or higher for identifying the type of a fine particle on the wafer, resulting in damage to the wafer. When irradiated with an electron beam, an organic fine particle on the wafer is decomposed into a carbon impurity which will remain on the wafer. Inasmuch as the fabrication of IC chips is carried out in an ultra-high clean room, the particle inspection apparatus itself is liable to cause contamination.

Due to the various above technical limitations, no practical particle inspection apparatus that can be used in the process of fabricating IC chips has been available in the art.

As described above, it takes more than 10 minutes to scan an 8-inch wafer in its entirety according to the Mie scattering inspection process, and it takes more than 5 minutes additionally to identify the type of a detected fine particle. The Mie scattering inspection process and the process for identifying the type of a detected fine particle cannot meet desired requirements for quick observation.

The EPMA and AES processes for identifying the type of fine particles are disadvantageous in that wafers under inspection are damaged by an electron beam for inspection, and the particle inspection apparatus itself tends to contaminate the clean room.

SUMMARY OF THE INVENTION

It is therefore an object of the present invention to provide a method of and an apparatus for detecting a surface condition of a wafer, which can practically be incorporated in a wafer fabrication system.

There has been desired a practical apparatus for detecting a fine particle on a wafer, which apparatus is capable of analyzing a wafer surface at a high speed and with high sensitivity, small in size and inexpensive to manufacture, will not serve as a source of contamination, and will not damage the wafer while analyzing same.

To avoid becoming a source of contamination, the apparatus is required to remove a wafer from a fabrication process, inspect the removed wafer to analyze contaminating fine particles quickly, and return the wafer back to the fabrication or line.

To accomplish the above object, there is provided in accordance with the present invention a method of detecting a surface condition of a wafer, comprising the steps of applying measuring light to a wafer from a reverse side thereof such that the measuring light undergoes total reflection from a surface of the wafer for thereby producing near-field leakage light on the surface of the wafer, and observing scattered light generated by said near-field leakage light to detect a surface condition of the wafer.

A phenomenon developed on the surface of the wafer may be determined based on a pattern of said scattered light.

Phenomena to be determined on the surface of the wafer may include a fine particle on the surface of the wafer, a surface irregularity of the surface of the wafer, and an IC pattern trench. The method may further comprise the step of comparing patterns of scattered light produced by the phenomena to be determined on the surface of the wafer with the pattern of said scattered light generated by the phenomenon thereby to determine the phenomenon developed on the surface of the wafer.

p-polarized light may be applied as said measuring light to produce said near-field leakage light as p-polarized light.

Alternatively, p-polarized light may be applied as said measuring light to produce said near-field leakage light as p-polarized light, s-polarized light may be applied as said measuring light to produce said near-field leakage light as s-polarized light, and the phenomenon developed on the surface of the wafer may be determined from a ratio between an intensity of first scattered light generated from said near-field leakage light as the p-polarized light at one spot on the surface of the wafer and an intensity of second scattered light generated from said near-field leakage light as the s-polarized light at said one spot.

The method may further comprise the step of comparing the intensity of the scattered light generated from said near-field leakage light as the p-polarized light at a spot on the surface of the wafer where a fine particle of metal has been judged as being present, with predetermined data to determine the type of metal of the fine particle at said spot.

According to the present invention, there is also provided an apparatus for detecting a surface condition of a wafer, comprising an X-Y stage for carrying a wafer thereon, a laser beam source for emitting a laser beam having a wavelength for transmission through said wafer, said laser beam source being positioned to apply said laser beam to said wafer from a reverse side thereof such that the laser beam undergoes total reflection from a surface of the wafer for thereby producing near-field leakage light on the surface of the wafer, a screen positioned such that scattered light generated by said near-field leakage light is projected onto said screen, an imaging device for imaging the scattered light projected onto said screen, a memory for storing patterns of scattered light produced by the phenomena and different combinations thereof on the surface of said wafer, and a controller for actuating said X-Y stage to scan said wafer with said laser beam and determining a surface condition of the wafer from a pattern of the scattered light imaged by said imaging device and said patterns of scattered light stored in said memory.

The phenomena may include a fine particle on the surface of the wafer, a surface irregularity of the surface of the wafer, and an IC pattern trench, and said controller may comprise means for comparing the stored patterns of scattered light produced by the phenomena with the pattern of said scattered light imaged by said imaging device to determine a phenomenon developed on the surface of the wafer.

The laser beam source may emit p-polarized light as said laser beam to produce said near-field leakage light as p-polarized light.

The laser beam source may comprise a first laser beam source for emitting p-polarized light as said laser beam to produce said near-field leakage light as p-polarized light, and a second laser beam source for emitting s-polarized light as said laser beam to produce said near-field leakage light as s-polarized light, and said controller may comprise means for determining a phenomenon developed on the surface of the wafer from a ratio between an intensity of first scattered light generated from said near-field leakage light as the p-polarized light at one spot on the surface of the wafer and an intensity of second scattered light generated from said near-field leakage light as the s-polarized light at said one spot.

The controller may comprise means for comparing the intensity of the first scattered light generated from said near-field leakage light as the p-polarized light at a spot on the surface of the wafer where a fine particle of metal has been judged as being present, with predetermined data to determine the type of metal of the fine particle at said spot.

The screen may be tilted with respect to the surface of the wafer at an angle ranging from 60° to 90°.

The principles of inspection according to the method of the present invention will be described below with reference to FIG. 1 of the accompanying drawings.

When light travels out of an Si wafer into air, the light can undergo total reflection. The critical angle θc, which is the smallest angle at which the total reflection occurs, is expressed by $$\sin \theta c = n_2/n_1$$

($n_1$, $n_2$ represent the refractive indexes of the Si wafer and air, respectively). Since the refractive index $n_1$ of the Si wafer is 1.5, the critical angle θc is 42 degrees. When a laser beam enters the Si wafer from its reverse side at an incident angle greater than the critical angle θc, the laser beam is subject to total reflection. As is known from the Goos Haenchen effect, the point where the light is totally reflected is displaced from the surface of the Si wafer by the wavelength ($\lambda_2$) of the incident light, as indicated in a region I in FIG. 1, and an evanescent wave is propagated over the surface of the Si wafer, the evanescent wave having a wavelength $$\lambda_e(=\lambda_2/\sin \theta c).$$

According to the present invention, light is applied to a wafer from the reverse side thereof and passed through the wafer, and near-field leakage light (evanescent wave) scattered by a fine particle on the surface of the wafer is utilized to detect the fine particle. If the wafer to be inspected is an Si wafer, then since the wavelength of light transmitted through the Si wafer is 1.1 μm or greater, near-infrared light is used as the light to be transmitted through the Si wafer.

The principles of observation according to the present invention will be described below with reference to FIGS. 2(a) and 2(b). Leakage light indicated as an evanescent wave 203 travels out of the surface of a wafer at a distance of about 1 μm, and is scattered by a fine particle 201 on the wafer and observed as scattered light indicated as a scattered wave 202. The scattered light has its scattering pattern varying depending on the shape of the fine particle 201.

If the shape of the fine particle 201 is spherical or vertically elongate with its longitudinal direction normal to the surface of the wafer, then the scattered light is intensive in both forward and backward directions of travel of the light in the wafer, as shown in FIG. 2(a). If the shape of the fine particle 201 is horizontally elongate with its longitudinal direction parallel to the surface of the wafer, then the scattered light is intensive in a direction normal to the surface of the wafer, as shown in FIG. 2(b).

The shape of fine particles on wafers can be identified on the basis of the above principles. It is known in the art that the intensity of the scattered light differs depending on whether the fine particle which scatters the light is of metal or not. See, for example, P. K. Aravind and H. Metiu: Surface Science 124 (1983) 550. R. Ruppin: Surface Science 127 (1983) 108.

As shown in FIG. 3 of the accompanying drawings, a fine particle 301 of metal on the surface of a wafer excites plasma oscillations to scatter incident near-field leakage light for thereby enhancing the leakage light, producing an expanded scattered wave 302 which is the scattered light with increased intensity. The above articles theoretically show that the intensity of light scattered by a fine particle of metal is more than 100 times the intensity of light scattered by a non-metal fine particle based on the above effect.

The method according to the present invention can theoretically be employed to detect fine particles regardless of the type of the fine particles. However, the method is considered to be highly sensitive particularly when used to detect fine particles of metal because of the above intensity pattern of scattered light.

The above and other objects, features, and advantages of the present invention will become apparent from the following description with reference to the accompanying drawings which illustrate examples of the present invention.

DETAILED DESCRIPTION OF THE PREFERRED EMBODIMENTS

1st Embodiment

Figure 1:
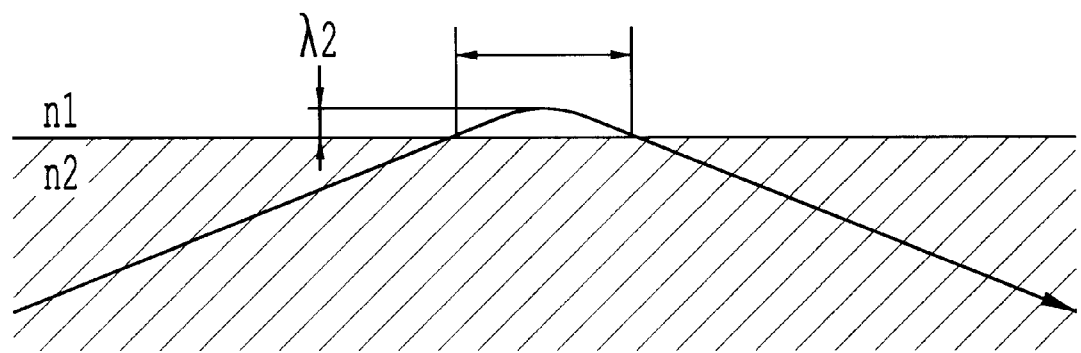
FIG. 1 is a diagram illustrative of the principles of inspection according to the present invention.
Figure 3:
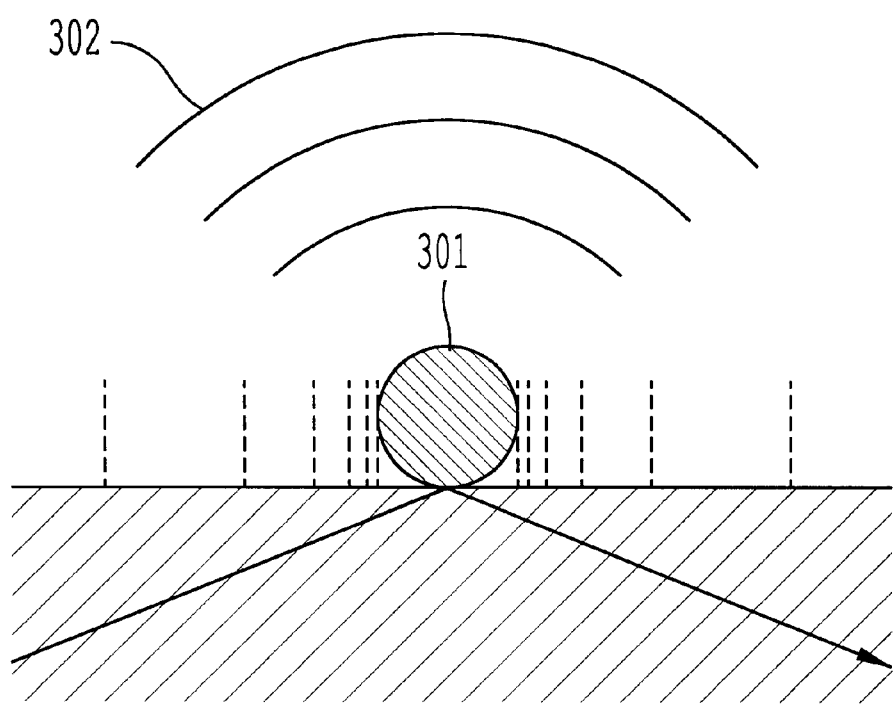
FIG. 3 is a diagram illustrative of the principles of observation according to the present invention.
Figure 2A:
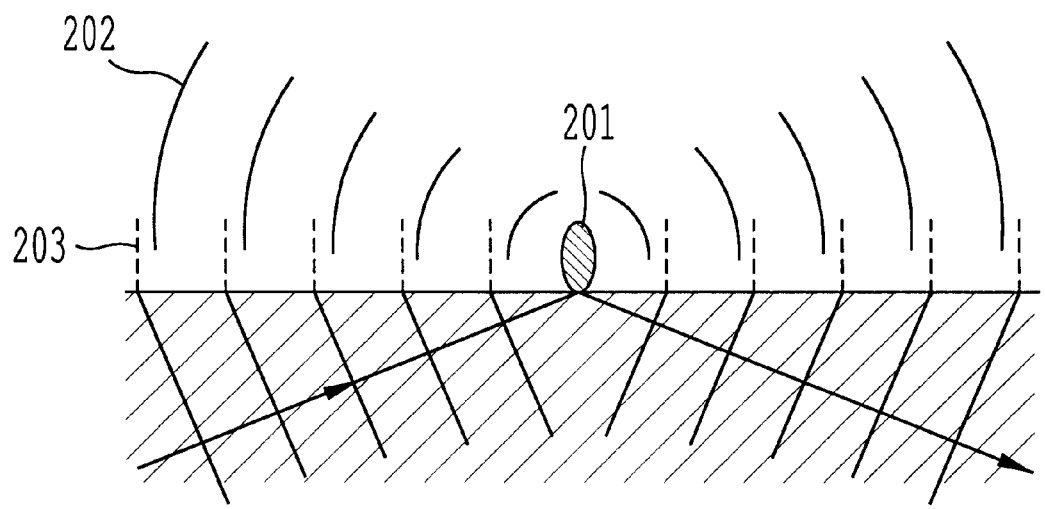
FIGS. 2(a) and 2(b) are diagrams illustrative of the principles of observation according to the present invention.
Figure 2B:
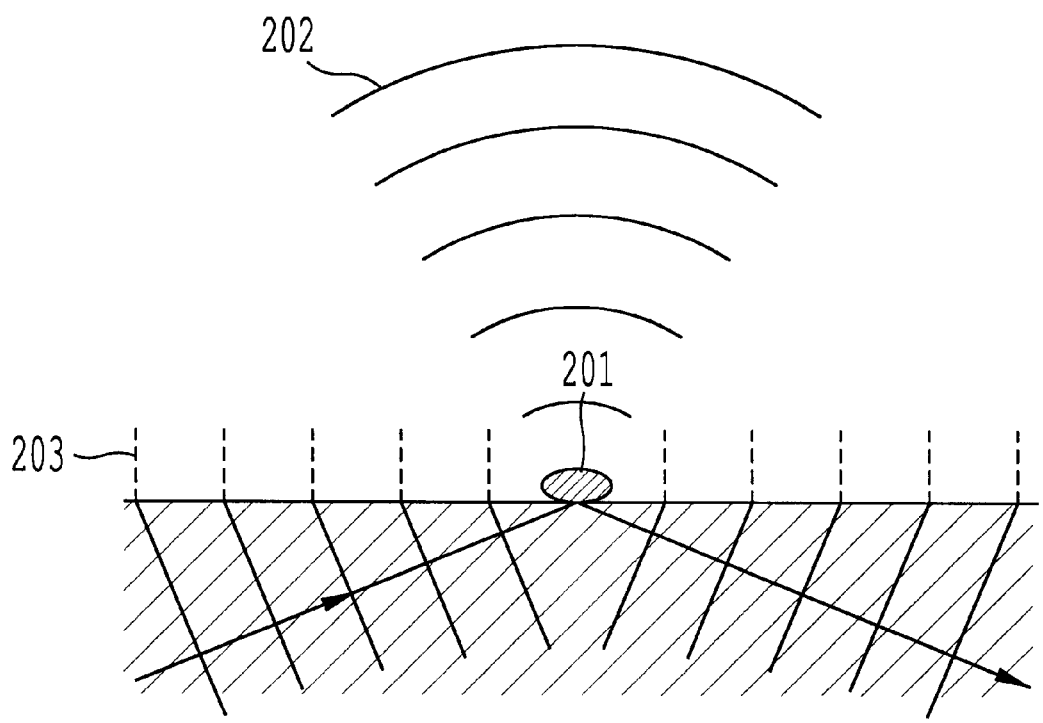
Figure 4:
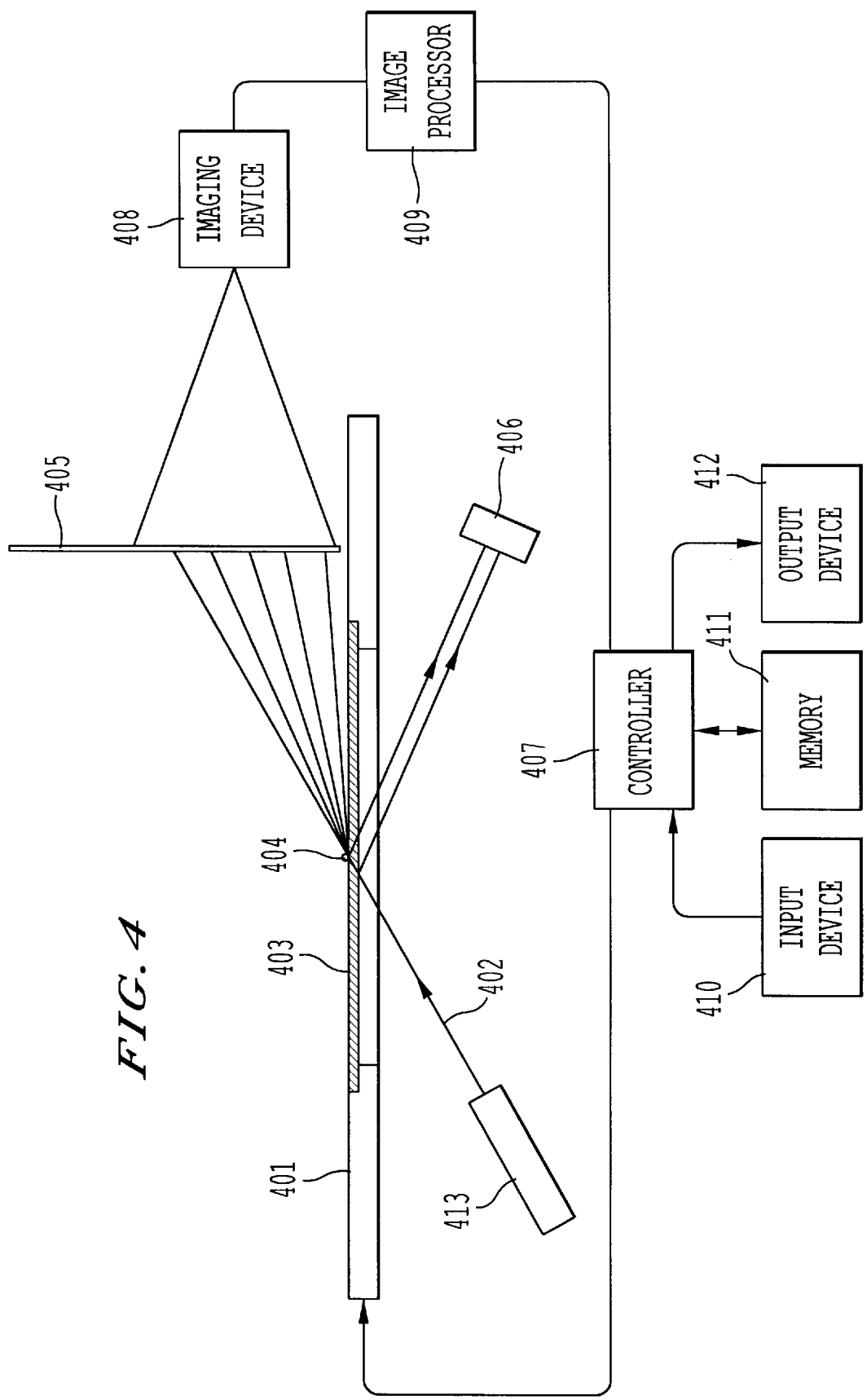
FIG. 4 is block diagram of an inspecting apparatus according to a embodiment of the present invention.

FIG. 4 shows in block form an inspecting apparatus according to an embodiment of the present invention.

The inspecting apparatus is installed in a clean room of a wafer fabrication room, and inspects a wafer in the atmosphere in the clean room.

As shown in FIG. 4, a wafer 403 to be inspected is placed on an X-Y stage 401 which can be moved at a high speed in X and Y directions.

A laser beam source 413 emits a near-infrared laser beam 402 having a wavelength of about 1.2 $\mu$m, to be applied to and transmitted through the wafer 403. The laser beam source 413 is fixedly positioned below the reverse side of the wafer 403 and oriented to direct the laser beam 402 toward the wafer 403 at such an incident angle that the laser beam 402 will undergo total reflection at the upper observed surface of the wafer 403. A lens system (not shown) for diverging or converging the laser beam 402 to cover an observed area of the wafer 403 is disposed between the laser beam source 413 and the wafer 403.

The X-Y stage 401 is movable at a high speed to enable the laser beam 402 to scan the observed surface of the wafer 403. If no fine particle is present on the observed surface of the wafer 403, then no scattered light is produced from the observed surface of the wafer 403. If there is a fine particle 404 present at a spot where the laser beam 402 is totally reflected by the observed surface of the wafer 403, then scattered light is produced from the observed surface of the wafer 403. A light absorber 406 for removing stray light is disposed below the X-Y stage 401 and on the path of a reflected laser beam from the wafer 403.

Scattered light is observed on a screen 405 positioned in the direction in which the scattered light travels, the screen 405 being semitransparent with respect to infrared light.

An image of the scattered light on the screen 405 is imaged by an imaging device 408 which comprises a near-infrared CCD camera, and converted by an image processor 409 into an image signal such as a video signal which is transmitted to a controller 407.

The controller 407 is connected to the image processor 409, an input device 410, a memory 411 for storing an operation program of the controller 407 and data necessary for analyzing images, and an output device 412. In response to commands entered from the input device 410, the controller 407 operates according to the program stored in the memory 411 to analyze the material, size, and shape of a fine particle based on the pattern and intensity of scattered light represented by an image signal sent from the image processor 409, outputs data representative of the analyzed material, size, and shape to the output device 412, which may comprise a printer, a display unit, etc., and actuates the X-Y stage 401 based on the analyzed material, size, and shape. The X-Y stage 401 may be actuated to reinspect those spots on the wafer 403 where fine particles are detected by scattered light, for example.

Wafers may have surface irregularities developed in masking and ion implantation processes, and may also have trenches produced by an etching process for forming an IC pattern. Since these surface irregularities and trenches disrupt total reflection conditions on the surface of the wafer 403, they can produce scattered light as is the case with fine particles.

Trenches produced on wafers for forming an IC pattern can be confirmed for their shapes and positions. When scattered light from wafers is observed, it is important from the standpoint of quality management to identify whether the scattered light is generated by a fine particle, a surface irregularity, or a trench.

Because a fine particle, a surface irregularity, and a trench (hereinafter referred to as "phenomena") on a wafer are different in shape from each other, patterns of scattered light produced thereby are also different from each other. Patterns of scattered light produced by different combinations of phenomena, e.g., a fine particle present on a surface irregularity, are also different from each other.

The memory 411 stores data representing patterns of scattered light produced by phenomena, and different combinations thereof. The controller 407 determines a surface condition of the wafer 403 by referring to the data stored in the memory 411.

Figure 5:
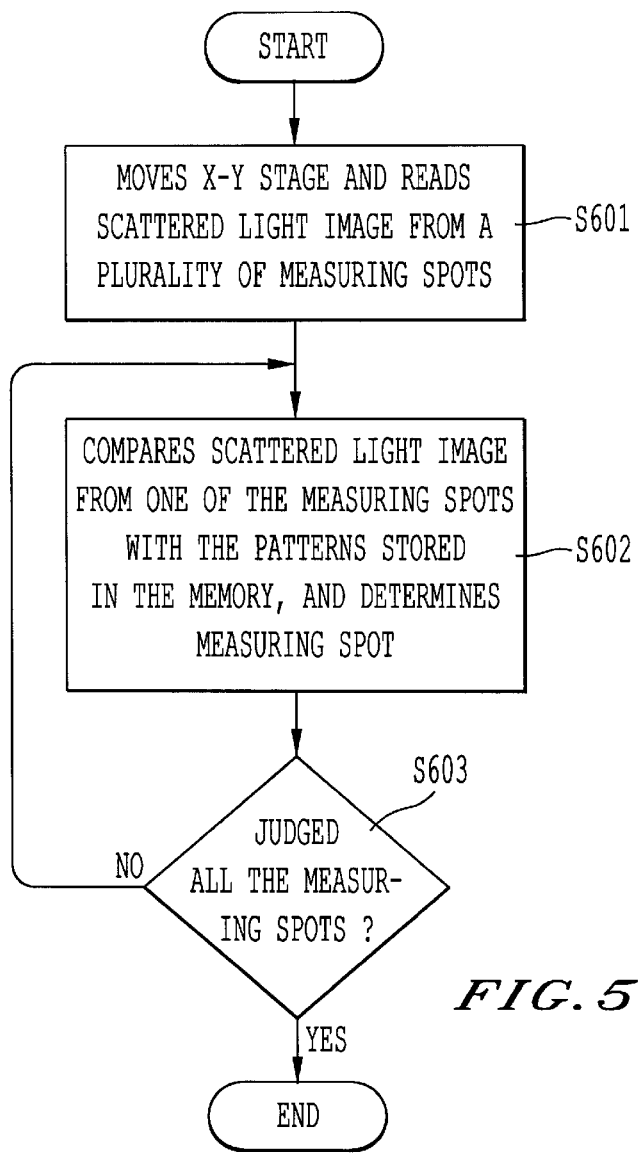
FIG. 5 is a flowchart of an operation sequence of a controller of the inspecting apparatus shown in FIG. 4 for detecting a surface condition of a wafer.

FIG. 5 shows an operation sequence of the controller 407 for detecting a surface condition of the wafer 403.

When the controller 407 starts to operate, the controller 407 moves the X-Y stage 401 to apply the laser beam 402 from the laser beam source 413 to the observed surface of the wafer 403, and reads scattered light images from a plurality of measuring spots on the wafer 403 in a step S601. Then, the controller 407 compares the scattered light image from one of the measuring spots with the patterns of scattered light stored in the memory 411, and determines the measuring spot whose scattered light image is closest to one of the patterns of scattered light as suffering the phenomenon which has produced the closest pattern of scattered light in a step S602. If no scattered light image is detected from one of the measuring spots, then the surface of the wafer 403 at the measuring spot is judged as normal. Thereafter, the controller 407 confirms whether it has judged all the measuring spots or not in a step S603. If all the measuring spots have been judged, then the operation sequence is ended. If there is or are measuring spots which have not been judged, then control returns to the step S602, and the steps S602, S603 are repeated.

In determining a surface condition of the wafer 403 based on patterns of scattered light according to the present invention, an optical system for observing patterns of scattered light plays an important role. In FIG. 4, the laser beam source 413 is oriented to direct the laser beam 402 toward the wafer 403 at such an incident angle that the laser beam 402 will undergo total reflection at the upper observed surface of the wafer 403. For efficient observation of scattered light, the angle at which the screen 405 is tilted with respect to the wafer 403 is prevalent, besides distance and dimensional considerations.

An experiment was conducted on various angles of tilt of the screen 405. As a result of the experiment, it was found out that scattered light images were well detected when the screen 405 was tilted with respect to the wafer 403 at an angle ranging from 60° to 90°, particularly in the vicinity of 80°, as confirmed from scattered light intensities and images. Therefore, the screen 405 should preferably be tilted with respect to the wafer 403 in such an angle range.

According to the present invention, as described above, the shape of a fine particle which has produced scattered light based on the Goos Haenchen effect is identified by observing the scattered light, and the type of the fine particle is identified based on the fact that the intensity of the scattered light is intensified by plasma oscillations which differ depending on the type of the fine particle. Specific embodiments of the present invention will be described below.

2nd Embodiment p-polarized leakage light whose electric field component of light lies in the plane of incidence and which has an electric field component perpendicular to the surface of the wafer is subject to resonance absorption by a fine particle of metal (a fine particle of metal which is not chemically bonded to the surface of the wafer, but held in weak contact with the surface of the wafer: a fine particle partly embedded in the leakage light electric field), intensifying the electric field of light on the surface of the fine particle for thereby producing intensive scattered light. s-polarized leakage light perpendicular to the p-polarized leakage light, however, is subject to almost no resonance absorption because its vibration mode does not comply with plasma oscillations, and does not intensify scattered light. Such intensification of scattered light is well known theoretically and experimentally.

The second embodiment is based on the fact that the intensity of scattered light varies depending on the polarized stage of a laser beam which is transmitted through a wafer and applied to a fine particle on the wafer.

Figure 6:
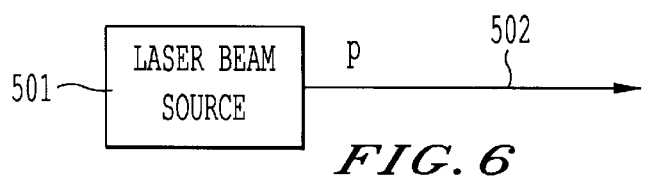
FIG. 6 is a block diagram of a laser beam source in an inspecting apparatus according to a second embodiment of the present invention.

FIG. 6 shows in block form a laser beam source in an inspecting apparatus according to a second embodiment of the present invention. The laser beam source, denoted at 501, emits a p-polarized laser beam as a measuring beam 502. Other details of the inspecting apparatus according to the second embodiment are identical to those of the inspecting apparatus according to the first embodiment shown in FIG. 4. The laser beam source 501 may comprise a resonator whose structure includes a means for limiting a polarized state. In the embodiment shown in FIG. 6, only p-polarized leakage light is generated from the wafer, efficiently intensifying scattered light produced by a fine particle of metal to allow the scattered light to be detected with increased sensitivity.

3rd Embodiment

Figure 7:
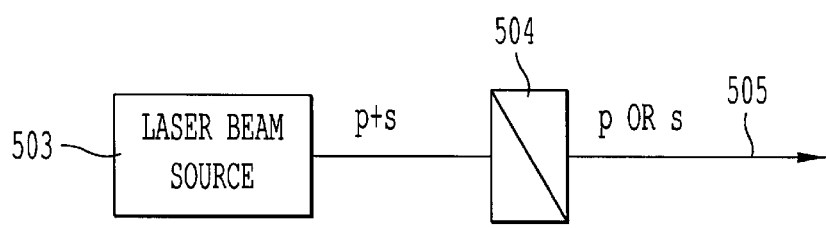
FIG. 7 is a block diagram of a laser beam source in an inspecting apparatus according to a third embodiment of the present invention.

FIG. 7 shows in block form a laser beam source in an inspecting apparatus according to a third embodiment of the present invention. According to the embodiment shown in FIG. 4, a phenomenon at a measuring spot is determined by the shape of scattered light produced by the phenomenon. According to the third embodiment shown in FIG. 7, however, the material of a fine particle on a wafer is identified based on the fact that the intensity of scattered light produced by a fine particle of metal from p-polarized leakage light is higher than the intensity of scattered light produced from an s-polarized leakage light.

As shown in FIG. 7, the inspecting apparatus includes a laser beam source 503 for emitting a laser beam containing both p-polarized light and s-polarized light, and a polarizer 504 for controlling the polarized state of the laser beam from the laser beam source 503 and emitting a measuring light 505. Other details of the inspecting apparatus according to the third embodiment are identical to those of the inspecting apparatus according to the first embodiment shown in FIG. 4.

According to the third embodiment, the controller 407 performs two measuring cycles for each measuring spot, i.e., a measuring cycle in which the laser beam source 503 emits a laser beam of p-polarized light only and a measuring cycle in which the laser beam source 503 emits a laser beam of s-polarized light only. The controller 407 compares the intensities of scattered light from each fine particle detected in the respective measuring cycles, and judges a fine particle detected when only a laser beam of p-polarized light is emitted or a fine particle from which scattered light is detected with higher sensitivity, as a fine particle of metal.

Figure 8:
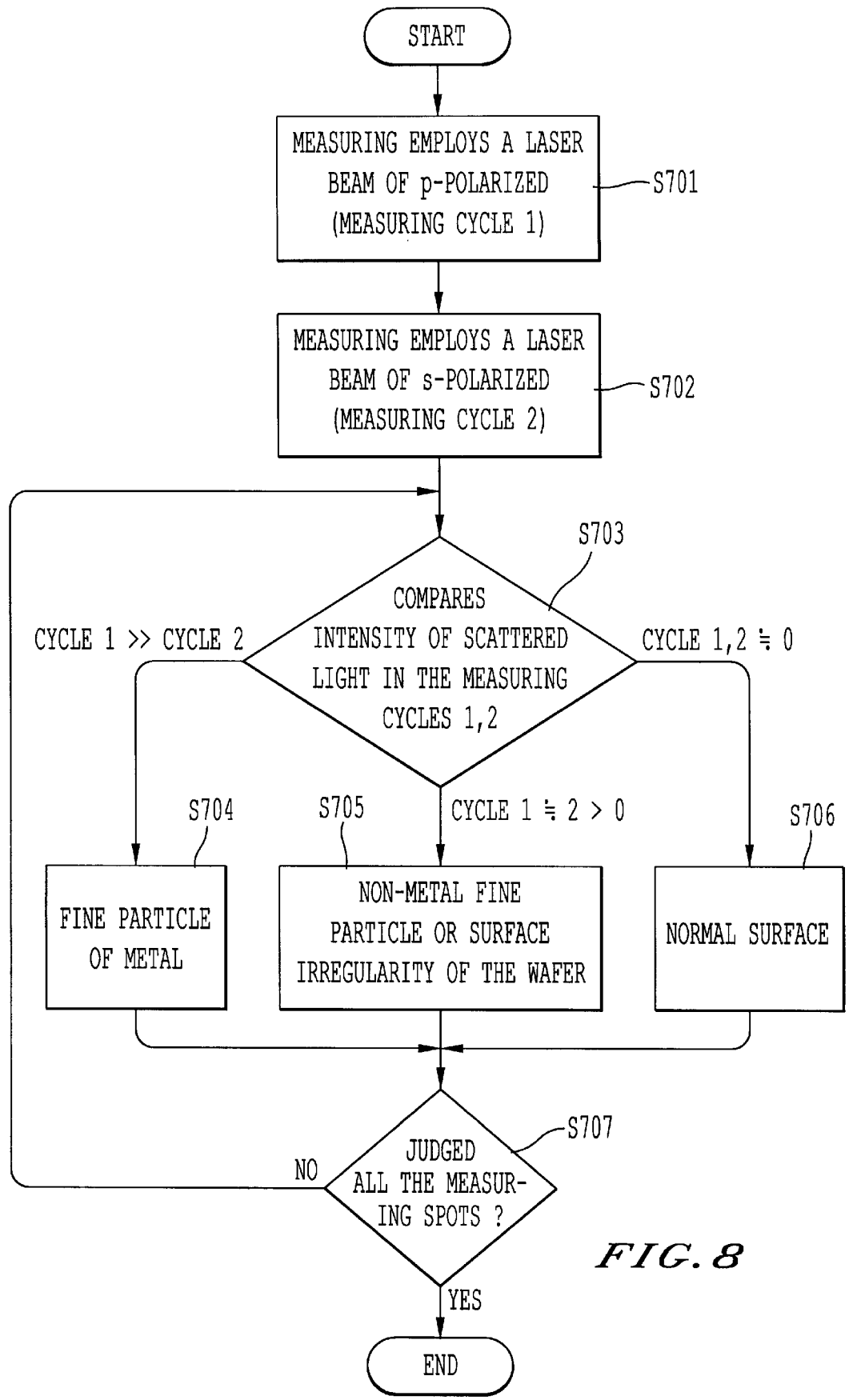
FIG. 8 is a flowchart of an operation sequence of the inspecting apparatus according to the third embodiment shown in FIG. 7.

FIG. 8 shows an operation sequence of the controller 407 of the inspecting apparatus according to the third embodiment shown in FIG. 7.

When a material identification process is started, the controller 407 carries out a measuring cycle which employs a laser beam of p-polarized light only (measuring cycle 1) and a measuring cycle which employs a laser beam of s-polarized light only (measuring cycle 2) for a certain measuring spot in respective steps S701, S702. These laser beams may be emitted from respective laser beam sources. Thereafter, the controller 407 compares intensities of scattered light produced by a fine particle on a wafer in the measuring cycles 1, 2 in a step S703. If the intensity of scattered light detected in the measuring cycle 1 is sufficiently higher than the intensity of scattered light detected in the measuring cycle 2, or only the intensity of scattered light is detected in the measuring cycle 1, then the controller 407 judges the fine particle as a fine particle of metal in a step S704. If the intensity of scattered light detected in the measuring cycle 1 and the intensity of scattered light detected in the measuring cycle 2 are substantially the same (0 or higher), then the controller 407 judges the fine particle as a non-metal fine particle or as a surface irregularity of the wafer in a step S705. If no scattered light is detected in either the measuring cycle 1 or the measuring cycle 2, then the controller 407 judges that the wafer has a normal surface which is free of surface irregularities and fine particles in a step S706. After the steps S704, S705, S706, the controller 407 confirms whether it has judged all the measuring spots or not in a step S707. If all the measuring spots have been judged, then the operation sequence is ended. If there is or are measuring spots which have not been judged, then control returns to the step S703, and the steps S703, S704, S705, S706, S707 are repeated.

The operation sequence of the controller 407 shown in FIG. 8 includes the step S703 of ascertaining whether the fine particle is a fine particle of metal or a non-metal fine particle or a surface irregularity, or the wafer has a normal surface. The same step may be carried out after the judging process shown in FIG. 5 with respect to only those measuring points which have been judged as containing a fine particle in the first embodiment shown in FIGS. 4 and 5. According to such a modification, it is possible to determine each of the phenomena, i.e., a fine particle of metal, a non-metal fine particle, a surface irregularity, an IC pattern trench, and combinations thereof, and the total number of times that the laser beam is applied to the wafer in two measuring cycles is reduced, making it possible to detect fine particles of metal quickly.

4th Embodiment

The plasma oscillations referred to above will be described in greater detail below. Plasma oscillations are defined as collective vibrations of free electrons in a metal. Free electrons have a lower energy level when they are vibrating than when they are at rest as a whole, and such a phenomenon is the same as zero-point vibrations of molecules. The plasma frequency is expressed by:

$$\omega_p^2 = 4\pi n e^2/m$$

where m represents the mass of an electron, n the density of free electrons, and e an electric charge. The surface plasma frequency at the surface of the metal is approximately expressed by:

$$\omega_{ps}^2 = 2\pi n e^2/m$$

The energy of surface plasma oscillations is lower than the energy of inner plasma oscillations.

If the frequency of near-infrared leakage light is indicated by $\omega$, then scattered light becomes more intensive as the frequency $\omega$ approaches a surface plasma frequency $\omega_{ps}$, and is the most intensive when $\omega = \omega_{ps}$.

The density n of free electrons in a metal differs depending on the type of the metal, the wavelength range in which plasma absorption occurs also differs depending on the type of the metal. For metals such as Cu, Ag whose density of free electrons is high, the wavelength range in which plasma absorption occurs is a blue range. For metals such as Fe, Ni, etc., plasma absorption occurs in a red range. Therefore, scattered light produced from near-infrared light by fine particles of Fe, Ni, etc., is more intensive than scattered light produced from near-infrared light by fine particles of Cu, etc.

As described above, when scattered light is observed at a single wavelength, the intensity of scattered light varies because the wavelength range in which plasma absorption occurs varies depending on the type of the metal. Stated otherwise, the type of a fine particle of metal which has been observed at a single wavelength can be identified by the intensity of the scattered light. The fourth embodiment is based on this principle.

The details of an inspecting apparatus according to a fourth embodiment of the present invention are identical to those of the inspecting apparatus according to the first embodiment shown in FIG. 4. However, the memory 411 stores a table of different metals and different plasma absorption wavelengths corresponding to the metals, as indicated below.

TABLE

| Metal Name | Plasma absorption wavelength |
|---|---|
| Metal 1 | λ1 |
| Metal 2 | λ2 |
| . | . |
| . | . |
| Metal n | λn |

Figure 9:
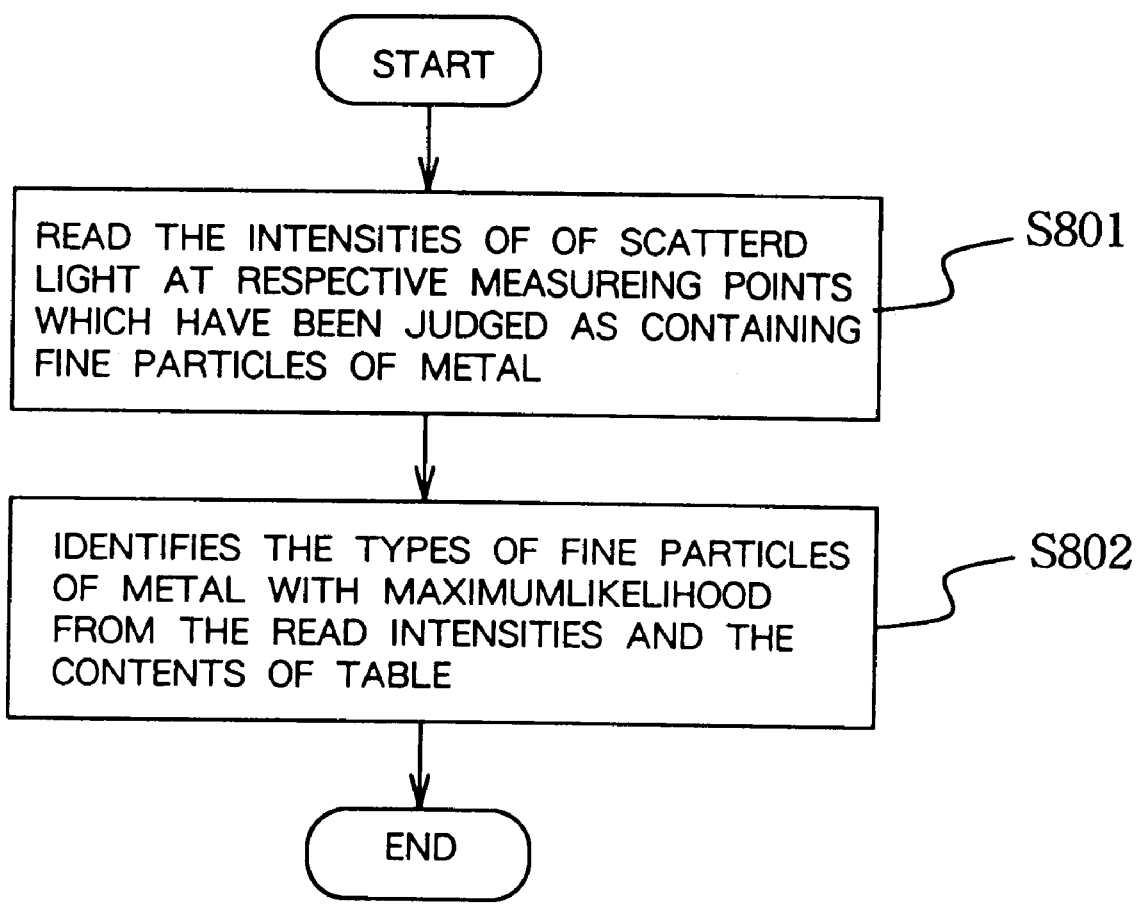
FIG. 9 is a flowchart of an operation sequence of an inspecting apparatus according to a fourth embodiment of the present invention.

FIG. 9 shows an operation sequence of the controller 407 of the inspecting apparatus according to the fourth embodiment of the present invention.

According to the fourth embodiment, the inspecting apparatus serves to identify the type of a fine particle of metal on a wafer. Prior to identifying the type of such a fine particle of metal, it is necessary to confirm the fine particle of metal on the wafer. Such a confirming process may be carried out by the operation sequence shown in FIG. 8 as described above.

In FIG. 9, after a fine particle of metal on a wafer has been confirmed, the controller 407 reads, in response to a command from the input device 410 to determine the type of fine particles of metal, the intensities of scattered light at respective measuring points which have been judged as containing fine particles of metal from the memory 411 in a step S801, and then identifies the types of fine particles of metal at the respective measuring points with maximum likelihood from the read intensities of scattered light and the contents of the above table stored in the memory 411 in a step S802.

Since the type identification with maximum likelihood in the step S802 is carried out based on the fact that the measuring light becomes more intensive as it approaches the plasma absorption wavelength, the measuring light may have one wavelength. The type identification may be performed more accurately by using a plurality of measuring lights having different wavelengths (e.g., 1.2 μm and 2.0 μm). The determining process shown in FIG. 5 and the determining process shown in FIG. 8 may also be carried out at a plurality of measuring light wavelengths.

A period of time required to effect measurements according to the present invention will be described below.

When an infrared laser beam is focused by a lens, the laser beam can be converged into a beam spot having a diameter of about 10 μm. Since an 8-inch wafer has a diameter of 200 mm, if the entire area of the 8-inch wafer were to be scanned with the beam spot having the diameter of 10 μm, a total of $4 \times 10^8$ observing spots would be needed on the wafer. It would practically be impossible to inspect the wafer at the $4 \times 10^8$ observing spots.

According to the present invention, the laser beam is successively converged into beam spots having diameters of 10 mm, 1 mm, 0.1 mm, and 0.01 mm (10 μm) by a lens system.

First, the entire area of the wafer is scanned with the beam spot having the diameter of 10 mm. If scattered light is observed from 1% of the wafer area (four observing spots), which is a maximum possible percentage of defects, then these four observing spots, each having a diameter of 10 mm, are scanned with the beam spot having the diameter of 1 mm. In this manner, the observing spots are inspected in successive inspecting cycles with progressively smaller beam spot diameters until they are inspected with the beam spot having the diameter of 10 μm.

If scattered light is observed from 1% of the area narrowed down in each of the inspecting cycles, then the entire wafer surface is finally observed at about 30,000 observing spots and 256 fine particles are determined. A period of about 20 msec. is required to inspect one observing spot, and hence a total period of 20 msec.×30,000=600 seconds=10 minutes is required to inspect the entire wafer area.

The above period of time is calculated on the assumption that maximum possible defects or fine particles are present on the wafer. Actually, therefore, the inspection of the wafer is expected to be completed in a shorter period of time.

With the arrangement of the present invention, unlike the conventional EPMA and AES processes used for identifying the type of fine particles of metal, phenomena on wafers, fine particles of metal, and types of fine particles of metal are determined from the data of patterns of scattered light stored in the memory and observed scattered light images. The period of time actually required for measurements according to the present invention is a period of time in which measuring light is applied to the wafer, and a subsequent detecting process is carried out by image processing. The inspecting apparatus according to the present invention is smaller in size and less expensive, and requires a shorter period of time than the conventional apparatus for inspecting wafers for fine particles with the Mie scattering process, the EPMA process, and the AES process, and can be installed in a wafer fabrication system.

While preferred embodiments of the present invention have been described using specific terms, such description is for illustrative purposes only, and it is to be understood that changes and variations may be made without departing from the spirit or scope of the following claims.

What is claimed is:

1. A method of detecting a surface condition of a wafer, comprising the steps of:

applying measuring light to a wafer from a reverse side thereof such that the measuring light undergoes total reflection from a surface of the wafer in order to produce near-field leakage light on the surface of the wafer;

observing a pattern of scattered light generated by said nearfield leakage light;

detecting a surface condition phenomena of the wafer based on the observed pattern of scattered light; and comparing predetermined patterns of scattered light with the observed pattern of scattered light in order to identify the surface condition phenomenon, wherein said comparing step comprises the steps of, comparing the observed pattern of scattered light to a predetermined pattern corresponding to a fine particle on the surface of the wafer, comparing the observed pattern of scattered light to a predetermined pattern corresponding to a surface irregularity of the surface of the wafer, and comparing the observed pattern of scattered light to a predetermined pattern corresponding to an IC pattern trench.

2. A method according to claim 1, wherein said step of applying comprises the step of:

applying p-polarized light in order to produce said near-field leakage light as p-polarized light.

3. A method according to claim 1, wherein said step of applying comprises the step of:

applying p-polarized light in order to produce said near-field leakage light as p-polarized light.

4. A method according to claim 1, wherein:

said step of applying comprises applying p-polarized light in order to produce said near-field leakage light as p-polarized light and applying s-polarized light in order to produce said near-field leakage light as s-polarized light; and said step of detecting comprises determining a ratio between an intensity of first scattered light generated from said near-field leakage light as the p-polarized light at one spot on the surface of the wafer and an intensity of second scattered light generated from said near-field leakage light as the s-polarized light at said one spot.

5. A method according to claim 4, wherein the detecting step further comprises the step of:

comparing the intensity of the scattered light generated from said near-field leakage light as the p-polarized light at a spot on the surface of the wafer where a fine particle of metal has been judged as being present with predetermined data to determine the type of metal of the fine particle at said spot.

6. An apparatus for detecting a surface condition of a wafer, comprising:

an X-Y stage for carrying a wafer thereon;

a laser beam source for emitting a laser beam having a wavelength for transmission through said wafer, said laser beam source being positioned to apply said laser beam to said wafer from a reverse side thereof such that the laser beam undergoes total reflection from a surface of the wafer for thereby producing near-field leakage light on the surface of the wafer;

a screen positioned such that scattered light generated by said near-field leakage light is projected onto said screen;

an imaging device for imaging the scattered light projected onto said screen;

a memory for storing patterns of scattered light produced by phenomena and different combinations thereof on the surface of said wafer; and a controller for actuating said X-Y stage to scan said wafer with said laser beam and determining a surface condition of the wafer from a pattern of the scattered light imaged by said imaging device and said patterns of scattered light stored in said memory.

7. An apparatus according to claim 6, wherein the phenomena include a fine particle on the surface of the wafer, a surface irregularity of the surface of the wafer, and an IC pattern trench, said controller comprising means for comparing the stored patterns of scattered light produced by the phenomena with the pattern of said scattered light imaged by said imaging device to determine a phenomenon developed on the surface of the wafer.

8. An apparatus according to claim 6, wherein said laser beam source emits p-polarized light as said laser beam to produce said near-field leakage light as p-polarized lights.

9. An apparatus according to claim 7, wherein said laser beam source emits p-polarized light as said laser beam to produce said near-field leakage light as p-polarized light.

10. An apparatus according to claim 6, wherein said laser beam source comprises a first laser beam source for emitting p-polarized light as said laser beam to produce said near-field leakage light as p-polarized light, and a second laser beam source for emitting s-polarized light as said laser beam to produce said near-field leakage light as s-polarized light, said controller comprising means for determining a phenomenon developed on the surface of the wafer a ratio between an intensity of first scattered light generated from said near-field leakage light as the p-polarized light at one spot on the surface of the wafer and an intensity of second scattered light generated from said near-field leakage light as the s-polarized light at said one spot.

11. An apparatus according to claim 7, wherein said controller comprises means for comparing the intensity of the first scattered light generated from said near-field leakage light as the p-polarized light at a spot on the surface of the wafer where a fine particle of metal has been judged as being present, with predetermined data to determine the type of metal of the fine particle at said spot.

12. An apparatus according to claim 6, wherein said screen is tilted with respect to the surface of the wafer at an angle ranging from 60° to 90°.

13. An apparatus according to claim 7, wherein said screen is tilted with respect to the surface of the wafer at an angle ranging from 60° to 90°.

14. An apparatus according to claim 8, wherein said screen is tilted with respect to the surface of the wafer at an angle ranging from 60° to 90°.

15. An apparatus according to claim 9, wherein said screen is tilted with respect to the surface of the wafer at an angle ranging from 60° to 90°.

16. An apparatus according to claim 10, wherein said screen is tilted with respect to the surface of the wafer at an angle ranging from 60° to 90°.

17. An apparatus according to claim 11, wherein said screen is tilted with respect to the surface of the wafer at an angle ranging from 60° to 90°.

* * * * *